(12) United States Patent
Stringham et al.

(10) Patent No.: US 10,357,306 B2
(45) Date of Patent: Jul. 23, 2019

(54) PLANAR FERROMAGNETIC COATED SURGICAL TIP AND METHOD FOR MAKING

(71) Applicant: Domain Surgical, Inc., Salt Lake City, UT (US)

(72) Inventors: Mark Stringham, Salt Lake City, UT (US); Robert R Scott, Salt Lake City, UT (US); Kent F Beck, Salt Lake City, UT (US); Phil Eggers, Salt Lake City, UT (US); Mel Lewis, Salt Lake City, UT (US)

(73) Assignee: Domain Surgical, Inc., Salt Lake City, UT (US)

( * ) Notice: Subject to any disclaimer, the term of this patent is extended or adjusted under 35 U.S.C. 154(b) by 408 days.

(21) Appl. No.: 14/711,662

(22) Filed: May 13, 2015

(65) Prior Publication Data

US 2015/0327907 A1  Nov. 19, 2015

Related U.S. Application Data

(60) Provisional application No. 61/996,741, filed on May 14, 2014.

(51) Int. Cl.
*A61B 18/08* (2006.01)
*C23C 30/00* (2006.01)
*A61B 18/00* (2006.01)
*A61B 17/00* (2006.01)
*A61B 18/14* (2006.01)

(52) U.S. Cl.
CPC .......... *A61B 18/085* (2013.01); *C23C 30/005* (2013.01); *A61B 2017/00526* (2013.01); *A61B 2017/00929* (2013.01); *A61B 2018/00071* (2013.01); *A61B 2018/00089* (2013.01); *A61B 2018/00148* (2013.01); *A61B 2018/00601* (2013.01); *A61B 2018/087* (2013.01); *A61B 2018/146* (2013.01)

(58) Field of Classification Search
CPC .................................................. A61B 18/085
See application file for complete search history.

(56) References Cited

U.S. PATENT DOCUMENTS

| 300,155 A | 6/1884 | Starr |
| 770,368 A | 9/1904 | Heath |
| 1,104,053 A | 7/1914 | Lea |

(Continued)

FOREIGN PATENT DOCUMENTS

| EP | 0033958 | 8/1981 |
| EP | 0 130 671 | 9/1985 |

(Continued)

OTHER PUBLICATIONS

Center for Research in Scientific Computation. *A Domain Wall Theory for Ferroelectric Hysteresis*, Jan. 1999.

(Continued)

*Primary Examiner* — Carl H Layno
*Assistant Examiner* — Jennifer L Ghand
(74) *Attorney, Agent, or Firm* — Cozen O'Connor (57) ABSTRACT

The present invention relates to surgical dissection tips comprising a substrate comprising beryllium copper and a ferromagnetic layer coating at least a portion of the substrate, and methods of making such surgical dissection tips.

26 Claims, 8 Drawing Sheets

(56) References Cited

U.S. PATENT DOCUMENTS

| | | |
|---|---|---|
| 1,280,052 A | 9/1918 | Lidberg |
| 1,335,987 A | 4/1920 | Reid |
| 1,366,231 A | 1/1921 | Winter et al. |
| 1,401,104 A | 12/1921 | Kruesheld |
| 1,794,296 A | 2/1931 | Hyams |
| 2,027,854 A | 1/1936 | Breth et al. |
| 2,050,904 A | 8/1936 | Trice |
| 2,120,598 A | 6/1938 | Beuoy |
| 2,250,602 A | 7/1941 | Pierce |
| 2,278,633 A | 4/1942 | Bagnall |
| 2,375,154 A | 5/1945 | Volterra |
| 2,412,977 A | 12/1946 | Eskin |
| 2,501,499 A | 3/1950 | Crowley |
| 2,670,425 A | 12/1954 | Stone |
| 2,735,797 A | 2/1956 | Schjeldahl |
| 2,782,290 A | 2/1957 | Lannan et al. |
| 2,831,242 A | 4/1958 | Kieffer et al. |
| 2,846,560 A | 8/1958 | Jacoby et al. |
| 2,863,036 A | 12/1958 | Mitchell et al. |
| 2,947,345 A | 8/1960 | Schjeldahl |
| 2,960,592 A | 11/1960 | Pierce |
| 3,084,242 A | 4/1963 | Vogler et al. |
| 3,213,259 A | 10/1965 | Bennet et al. |
| 3,350,544 A | 10/1967 | Lennox |
| 3,352,011 A | 11/1967 | Alexander et al. |
| 3,400,252 A | 9/1968 | Hayakawa |
| 3,404,202 A | 10/1968 | Carlson et al. |
| 3,413,442 A | 11/1968 | Buiting et al. |
| 3,414,705 A | 12/1968 | Marcoux |
| 3,434,476 A | 3/1969 | Shaw et al. |
| 3,501,619 A | 3/1970 | Buiting et al. |
| 3,515,837 A | 6/1970 | Ando |
| 3,520,043 A | 7/1970 | Darling |
| 3,556,953 A | 1/1971 | Schulz |
| 3,768,482 A | 10/1973 | Shaw |
| 3,825,004 A | 7/1974 | Durden, III |
| 3,826,263 A | 7/1974 | Cage et al. |
| 3,834,392 A | 9/1974 | Lampman et al. |
| 3,978,312 A | 8/1976 | Barton et al. |
| RE29,088 E | 12/1976 | Shaw |
| 4,089,336 A | 5/1978 | Cage et al. |
| 4,091,813 A | 5/1978 | Shaw et al. |
| RE30,190 E | 1/1980 | Shaw |
| 4,185,632 A | 1/1980 | Shaw |
| 4,196,734 A | 4/1980 | Harris |
| 4,198,957 A | 4/1980 | Cage et al. |
| 4,206,759 A | 6/1980 | Shaw |
| 4,207,896 A | 6/1980 | Shaw |
| 4,209,017 A | 6/1980 | Shaw |
| 4,256,945 A | 3/1981 | Carter et al. |
| 4,359,052 A | 11/1982 | Staub |
| 4,364,390 A | 12/1982 | Shaw |
| 4,371,861 A | 2/1983 | Abdelrahman et al. |
| 4,374,517 A | 2/1983 | Hagiwara |
| RE31,723 E | 11/1984 | Shaw |
| 4,481,057 A | 11/1984 | Beard |
| 4,485,810 A | 12/1984 | Beard |
| 4,492,231 A | 1/1985 | Auth |
| 4,493,320 A | 1/1985 | Treat |
| 4,523,084 A | 6/1985 | Tamura et al. |
| 4,549,073 A | 10/1985 | Tamura et al. |
| 4,600,018 A | 7/1986 | James et al. |
| 4,622,966 A | 11/1986 | Beard |
| 4,658,819 A | 4/1987 | Harris et al. |
| 4,658,820 A | 4/1987 | Klicek |
| 4,701,587 A | 10/1987 | Carter et al. |
| 4,752,673 A | 6/1988 | Krumme |
| 4,807,620 A | 2/1989 | Strul |
| 4,839,501 A | 6/1989 | Cowell |
| 4,848,337 A | 7/1989 | Shaw et al. |
| 4,860,745 A | 8/1989 | Farin et al. |
| 4,877,944 A | 10/1989 | Cowell et al. |
| 4,914,267 A | 4/1990 | Derbyshire |
| 4,915,100 A | 4/1990 | Green |
| 4,927,413 A | 5/1990 | Hess |
| 4,938,761 A | 7/1990 | Ensslin |
| 5,003,991 A | 4/1991 | Takayama et al. |
| 5,047,025 A | 9/1991 | Taylor et al. |
| 5,053,595 A | 10/1991 | Derbyshire |
| 5,057,106 A | 10/1991 | Kasevich et al. |
| 5,071,419 A | 12/1991 | Rydell et al. |
| 5,087,256 A | 2/1992 | Taylor et al. |
| 5,087,804 A | 2/1992 | McGaffigan |
| 5,098,429 A | 3/1992 | Sterzer |
| 5,107,095 A | 4/1992 | Derbyshire |
| 5,125,927 A | 6/1992 | Belanger |
| 5,182,427 A | 1/1993 | McGaffigan |
| 5,189,271 A | 2/1993 | Derbyshire |
| 5,197,649 A | 3/1993 | Bessler et al. |
| 5,203,782 A | 4/1993 | Gudov et al. |
| 5,209,725 A | 5/1993 | Roth |
| 5,211,646 A | 5/1993 | Alperovich et al. |
| 5,217,460 A | 9/1993 | Knoepfler |
| 5,300,068 A | 4/1994 | Rosar et al. |
| 5,300,750 A | 4/1994 | Carter, Jr. et al. |
| 5,308,311 A | 5/1994 | Eggers et al. |
| 5,318,564 A | 6/1994 | Eggers |
| 5,364,392 A | 11/1994 | Warner et al. |
| 5,370,645 A | 12/1994 | Klicek et al. |
| 5,370,675 A | 12/1994 | Edwards et al. |
| 5,376,094 A | 12/1994 | Kline |
| 5,382,247 A | 1/1995 | Cimino et al. |
| 5,400,267 A | 3/1995 | Denen et al. |
| 5,411,508 A | 5/1995 | Bessler et al. |
| 5,423,808 A | 6/1995 | Edwards et al. |
| 5,425,731 A | 6/1995 | Daniel et al. |
| 5,445,635 A | 8/1995 | Denen et al. |
| 5,472,443 A | 12/1995 | Cordis et al. |
| 5,475,203 A | 12/1995 | McGaffigan |
| 5,480,397 A | 1/1996 | Eggers |
| 5,480,398 A | 1/1996 | Eggers |
| 5,496,312 A | 3/1996 | Klicek |
| 5,496,314 A | 3/1996 | Eggers |
| 5,507,743 A | 4/1996 | Edwards et al. |
| 5,540,679 A | 7/1996 | Fram et al. |
| 5,540,681 A | 7/1996 | Strul et al. |
| 5,542,916 A | 8/1996 | Hirsch et al. |
| 5,571,153 A | 11/1996 | Wallsten |
| 5,573,533 A | 11/1996 | Strul |
| 5,593,406 A | 1/1997 | Eggers et al. |
| 5,595,565 A | 1/1997 | Treat et al. |
| 5,611,798 A | 3/1997 | Eggers |
| 5,628,771 A | 5/1997 | Mizukawa et al. |
| 5,674,219 A | 10/1997 | Monson et al. |
| 5,707,369 A | 1/1998 | Vaitekunas et al. |
| 5,707,402 A | 1/1998 | Heim |
| 5,807,392 A | 9/1998 | Eggers |
| 5,807,393 A | 9/1998 | Williamson, IV et al. |
| 5,827,269 A | 10/1998 | Saadat |
| 5,836,874 A | 11/1998 | Swanson et al. |
| 5,836,943 A | 11/1998 | Miller, III |
| 5,843,019 A | 12/1998 | Eggers et al. |
| 5,855,061 A * | 1/1999 | Malis .................... A61B 18/14 219/233 |
| 5,911,719 A | 6/1999 | Eggers |
| 5,951,546 A | 9/1999 | Lorentzen |
| 5,964,759 A | 10/1999 | Yamanashi et al. |
| 6,004,316 A | 12/1999 | Laufer |
| 6,006,755 A | 12/1999 | Edwards |
| 6,015,415 A | 1/2000 | Avellanet |
| 6,030,381 A * | 2/2000 | Jones ................. A61B 18/1402 606/33 |
| 6,035,238 A | 3/2000 | Ingle et al. |
| 6,038,017 A | 3/2000 | Pinsukanjana et al. |
| 6,039,733 A | 3/2000 | Buysse et al. |
| 6,066,138 A | 5/2000 | Sheffer et al. |
| 6,161,048 A | 12/2000 | Sluijter et al. |
| 6,190,382 B1 | 2/2001 | Ormsby et al. |
| 6,210,403 B1 | 4/2001 | Klicek |
| 6,228,084 B1 | 5/2001 | Kirwan, Jr. |
| 6,241,723 B1 | 6/2001 | Heim et al. |
| 6,287,305 B1 | 9/2001 | Heim et al. |
| 6,290,697 B1 | 9/2001 | Tu et al. |
| 6,350,262 B1 | 2/2002 | Ashley |

(56) References Cited

U.S. PATENT DOCUMENTS

| | | |
|---|---|---|
| 6,358,273 B1 | 3/2002 | Strul et al. |
| 6,454,781 B1 | 9/2002 | Witt et al. |
| 6,533,781 B2 | 3/2003 | Heim et al. |
| 6,602,252 B2 | 8/2003 | Mollenauer |
| 6,604,003 B2 | 8/2003 | Fredricks et al. |
| 6,626,901 B1 | 9/2003 | Treat et al. |
| 6,632,182 B1 | 10/2003 | Treat |
| 6,692,489 B1 | 2/2004 | Heim et al. |
| 6,723,094 B1 | 4/2004 | DeSinger |
| 6,726,683 B1 | 4/2004 | Shaw |
| 6,821,273 B2 | 11/2004 | Mollenauer |
| 6,860,880 B2 | 3/2005 | Treat et al. |
| 6,908,463 B2 | 6/2005 | Treat et al. |
| 6,911,026 B1 | 6/2005 | Hall et al. |
| 6,912,911 B2 | 7/2005 | Oh et al. |
| 6,980,862 B2 | 12/2005 | Fredricks et al. |
| 6,980,865 B1 | 12/2005 | Wang et al. |
| 7,011,656 B2 | 3/2006 | McGaffigan |
| 7,025,065 B2 | 4/2006 | McGaffigan et al. |
| 7,083,613 B2 | 8/2006 | Treat |
| 7,112,201 B2 | 9/2006 | Truckai et al. |
| 7,122,030 B2 | 10/2006 | Flores et al. |
| 7,164,968 B2 | 1/2007 | Treat et al. |
| 7,175,621 B2 | 2/2007 | Heim et al. |
| 7,211,079 B2 | 5/2007 | Treat |
| 7,211,080 B2 | 5/2007 | Treat et al. |
| 7,235,073 B2 | 6/2007 | Levine et al. |
| 7,300,452 B2 | 11/2007 | Gleich |
| 7,317,275 B2 | 1/2008 | Treat |
| 7,326,202 B2 | 2/2008 | McGaffigan |
| 7,329,255 B2 | 2/2008 | McGaffigan |
| 7,377,919 B2 | 5/2008 | Heim et al. |
| 7,396,356 B2 | 7/2008 | Mollenauer |
| 7,435,249 B2 | 10/2008 | Buysse et al. |
| 7,473,250 B2 | 1/2009 | Makin et al. |
| 7,473,253 B2 | 1/2009 | Dycus et al. |
| 7,494,492 B2 | 2/2009 | Da Silva et al. |
| 7,528,663 B2 | 5/2009 | Naletov et al. |
| 7,533,719 B2 | 5/2009 | Hinson |
| 7,540,324 B2 | 6/2009 | de Rouffignac |
| 7,549,470 B2 | 6/2009 | Vinegar |
| 7,553,309 B2 | 6/2009 | Buysse et al. |
| 7,556,095 B2 | 7/2009 | Vinegar |
| 7,556,096 B2 | 7/2009 | Vinegar |
| 7,559,367 B2 | 7/2009 | Vinegar |
| 7,559,368 B2 | 7/2009 | Vinegar |
| 7,562,706 B2 | 7/2009 | Li et al. |
| 7,562,707 B2 | 7/2009 | Miller |
| 7,578,815 B2 | 8/2009 | Howell |
| 7,581,589 B2 | 9/2009 | Roes et al. |
| 7,584,789 B2 | 9/2009 | Mo et al. |
| 7,588,565 B2 | 9/2009 | Marchitto et al. |
| 7,588,566 B2 | 9/2009 | Treat et al. |
| 7,591,310 B2 | 9/2009 | Minderhoud |
| 7,597,147 B2 | 10/2009 | Vitek |
| 7,604,052 B2 | 10/2009 | Roes |
| 7,610,962 B2 | 11/2009 | Fowler |
| 7,613,523 B2 | 11/2009 | Eggers et al. |
| 7,631,689 B2 | 12/2009 | Vinegar |
| 7,631,690 B2 | 12/2009 | Vinegar |
| 7,632,295 B2 | 12/2009 | Flores |
| 7,635,023 B2 | 12/2009 | Goldberg |
| 7,635,024 B2 | 12/2009 | Karanikas |
| 7,635,025 B2 | 12/2009 | Vinegar |
| 7,678,105 B2 | 3/2010 | McGreevy et al. |
| 7,699,842 B2 | 4/2010 | Buysse et al. |
| 7,702,397 B2 | 4/2010 | Fredricks et al. |
| 7,776,035 B2 | 8/2010 | Rick et al. |
| 7,828,798 B2 | 11/2010 | Buysse et al. |
| 7,871,406 B2 | 1/2011 | Nields et al. |
| 7,879,033 B2 | 2/2011 | Sartor et al. |
| 7,887,535 B2 | 2/2011 | Lands et al. |
| 7,922,713 B2 | 4/2011 | Geisel |
| 7,931,649 B2 | 4/2011 | Couture et al. |
| 7,938,779 B2 | 5/2011 | Sakurai et al. |
| 7,951,149 B2 | 5/2011 | Carlton |
| 7,951,150 B2 | 5/2011 | Johnson et al. |
| 7,959,633 B2 | 6/2011 | Sartor et al. |
| 7,963,965 B2 | 6/2011 | Buysse et al. |
| 7,972,334 B2 | 7/2011 | McGreevy et al. |
| 7,972,335 B2 | 7/2011 | McGreevy et al. |
| 7,981,113 B2 | 7/2011 | Truckai et al. |
| 8,062,290 B2 | 11/2011 | Buysse et al. |
| 8,100,896 B2 | 1/2012 | Rodhajsky |
| 8,100,908 B2 | 1/2012 | McGaffigan et al. |
| 8,104,956 B2 | 1/2012 | Blaha |
| 8,105,323 B2 | 1/2012 | Buysse et al. |
| 8,211,105 B2 | 7/2012 | Buysse et al. |
| 8,241,284 B2 | 8/2012 | Dycus et al. |
| 8,287,528 B2 | 10/2012 | Wham et al. |
| 8,292,879 B2 | 10/2012 | Manwaring et al. |
| 8,372,066 B2 | 2/2013 | Manwaring et al. |
| 8,377,052 B2 | 2/2013 | Manwaring et al. |
| 8,377,057 B2 | 2/2013 | Rick et al. |
| 8,414,569 B2 | 4/2013 | Manwaring et al. |
| 8,419,724 B2 | 4/2013 | Manwaring et al. |
| 8,425,503 B2 | 4/2013 | Manwaring et al. |
| 8,430,870 B2 | 4/2013 | Manwaring et al. |
| 8,460,870 B2 | 6/2013 | Zocchi |
| 8,480,666 B2 | 7/2013 | Buysse et al. |
| 8,491,578 B2 | 7/2013 | Manwaring et al. |
| 8,506,561 B2 | 8/2013 | Manwaring et al. |
| 8,523,850 B2 | 9/2013 | Manwaring et al. |
| 8,523,851 B2 | 9/2013 | Manwaring et al. |
| 8,568,402 B2 | 10/2013 | Buysse et al. |
| 8,617,151 B2 | 12/2013 | Manwaring et al. |
| 8,667,674 B2 | 3/2014 | Buysse |
| 8,672,938 B2 | 3/2014 | Buysse et al. |
| 2001/0014804 A1 | 8/2001 | Goble et al. |
| 2002/0019627 A1 | 2/2002 | Maguire et al. |
| 2002/0019644 A1 | 2/2002 | Hastings et al. |
| 2002/0026188 A1 | 2/2002 | Balbierz et al. |
| 2002/0029037 A1 | 3/2002 | Kim |
| 2002/0029062 A1 | 3/2002 | Satake |
| 2002/0068931 A1 | 6/2002 | Wong et al. |
| 2002/0087156 A1 | 7/2002 | Maguire et al. |
| 2002/0120261 A1 | 8/2002 | Balbierz et al. |
| 2002/0133148 A1 | 9/2002 | Daniel et al. |
| 2002/0165529 A1 | 11/2002 | Danek |
| 2002/0173787 A1 | 11/2002 | Buysse et al. |
| 2003/0004507 A1 | 1/2003 | Francischelli et al. |
| 2003/0055417 A1 | 3/2003 | Truckai et al. |
| 2003/0055424 A1 | 3/2003 | Ciarrocca |
| 2003/0060818 A1 | 3/2003 | Kannenberg et al. |
| 2003/0073987 A1 | 4/2003 | Sakurai et al. |
| 2003/0073989 A1 | 4/2003 | Hoey et al. |
| 2003/0109871 A1 | 6/2003 | Johnson et al. |
| 2003/0139741 A1 | 7/2003 | Goble et al. |
| 2003/0144660 A1 | 7/2003 | Mollenauer |
| 2003/0171747 A1 | 9/2003 | Kanehira et al. |
| 2003/0176873 A1 | 9/2003 | Chernenko et al. |
| 2003/0195499 A1 | 10/2003 | Prakash et al. |
| 2003/0199755 A1 | 10/2003 | Halperin |
| 2003/0208199 A1 | 11/2003 | Keane |
| 2003/0212389 A1 | 11/2003 | Durgin et al. |
| 2004/0006335 A1 | 1/2004 | Garrison |
| 2004/0030330 A1 | 2/2004 | Brassell et al. |
| 2004/0034349 A1 | 2/2004 | Kirwan, Jr. et al. |
| 2004/0049185 A1 | 3/2004 | Latterell et al. |
| 2004/0059345 A1 | 3/2004 | Nakao et al. |
| 2004/0073256 A1 | 4/2004 | Marchitto |
| 2004/0167506 A1 | 8/2004 | Chen |
| 2004/0176756 A1 | 9/2004 | McGaffigan |
| 2004/0187875 A1 | 9/2004 | He et al. |
| 2004/0243120 A1 | 12/2004 | Orszulak et al. |
| 2005/0021016 A1 | 1/2005 | Malecki et al. |
| 2005/0033338 A1 | 2/2005 | Ferree |
| 2005/0072827 A1 | 4/2005 | Mollenauer |
| 2005/0090817 A1 | 4/2005 | Phan |
| 2005/0107776 A1 | 5/2005 | Mcgaffigan et al. |
| 2005/0113824 A1 | 5/2005 | Sartor et al. |
| 2005/0197661 A1 | 9/2005 | Carrison et al. |
| 2005/0245919 A1 | 11/2005 | Van der Welde |
| 2005/0273111 A1 | 12/2005 | Ferree et al. |

(56) References Cited

U.S. PATENT DOCUMENTS

| | | |
|---|---|---|
| 2005/0283067 A1 | 12/2005 | Sobe |
| 2005/0283149 A1 | 12/2005 | Thorne et al. |
| 2005/0288659 A1 | 12/2005 | Kimura et al. |
| 2006/0004356 A1 | 1/2006 | Bilski et al. |
| 2006/0127706 A1 | 6/2006 | Goebel et al. |
| 2006/0142824 A1 | 6/2006 | Zikorus et al. |
| 2006/0161149 A1 | 7/2006 | Privitera et al. |
| 2006/0167450 A1 | 7/2006 | Johnson et al. |
| 2006/0212030 A1 | 9/2006 | McGaffigan |
| 2006/0212031 A1 | 9/2006 | McGaffigan et al. |
| 2006/0217700 A1 | 9/2006 | Garito et al. |
| 2006/0217706 A1 | 9/2006 | Lau et al. |
| 2006/0241587 A1 | 10/2006 | Heim et al. |
| 2006/0241588 A1 | 10/2006 | Heim et al. |
| 2006/0241589 A1 | 10/2006 | Heim et al. |
| 2006/0271037 A1 | 11/2006 | Maroney et al. |
| 2006/0287649 A1 | 12/2006 | Ormsby et al. |
| 2007/0005054 A1 | 1/2007 | Heim et al. |
| 2007/0005055 A1 | 1/2007 | Heim et al. |
| 2007/0005056 A1 | 1/2007 | Heim et al. |
| 2007/0005057 A1 | 1/2007 | Heim et al. |
| 2007/0005058 A1 | 1/2007 | Heim et al. |
| 2007/0005059 A1 | 1/2007 | Heim et al. |
| 2007/0005060 A1 | 1/2007 | Heim et al. |
| 2007/0016181 A1 | 1/2007 | van der Weide et al. |
| 2007/0016272 A1 | 1/2007 | Thompson et al. |
| 2007/0060920 A1 | 3/2007 | Weitzner |
| 2007/0073282 A1 | 3/2007 | McGaffigan et al. |
| 2007/0100336 A1 | 5/2007 | McFarlin et al. |
| 2007/0100405 A1 | 5/2007 | Thompson et al. |
| 2007/0106294 A1 | 5/2007 | Nesbitt |
| 2007/0127897 A1 | 6/2007 | John et al. |
| 2007/0131428 A1 | 6/2007 | Boestert |
| 2007/0173811 A1 | 7/2007 | Couture et al. |
| 2007/0208339 A1 | 9/2007 | Arts et al. |
| 2007/0219544 A1 | 9/2007 | Gowda |
| 2007/0239151 A1 | 10/2007 | Atalar et al. |
| 2007/0270924 A1 | 11/2007 | McCann et al. |
| 2008/0017380 A1 | 1/2008 | Vinegar |
| 2008/0033419 A1 | 2/2008 | Nields et al. |
| 2008/0035346 A1 | 2/2008 | Nair et al. |
| 2008/0035347 A1 | 2/2008 | Brady |
| 2008/0035705 A1 | 2/2008 | Menotti |
| 2008/0038144 A1 | 2/2008 | Maziasz |
| 2008/0077129 A1 | 3/2008 | Van Wyk et al. |
| 2008/0119841 A1 | 5/2008 | Geisel |
| 2008/0128134 A1 | 6/2008 | Mudunuri et al. |
| 2008/0135253 A1 | 6/2008 | Vinegar |
| 2008/0135254 A1 | 6/2008 | Vinegar |
| 2008/0142216 A1 | 6/2008 | Vinegar |
| 2008/0142217 A1 | 6/2008 | Pieterson |
| 2008/0161800 A1 | 7/2008 | Wang et al. |
| 2008/0173444 A1 | 7/2008 | Stone et al. |
| 2008/0174115 A1 | 7/2008 | Lambirth |
| 2008/0185147 A1 | 8/2008 | Vinegar |
| 2008/0187989 A1 | 8/2008 | McGreevy et al. |
| 2008/0217003 A1 | 9/2008 | Kuhlman |
| 2008/0217016 A1 | 9/2008 | Stegemeier |
| 2008/0228135 A1 | 9/2008 | Snoderly |
| 2008/0236831 A1 | 10/2008 | Hsu |
| 2008/0255642 A1 | 10/2008 | Zarins et al. |
| 2008/0277113 A1 | 11/2008 | Stegemeier |
| 2008/0281310 A1 | 11/2008 | Dunning et al. |
| 2008/0281315 A1 | 11/2008 | Gines |
| 2008/0281386 A1 | 11/2008 | Herbette et al. |
| 2008/0319438 A1 | 12/2008 | DeCarlo |
| 2009/0014180 A1 | 1/2009 | Stegemeier |
| 2009/0014181 A1 | 1/2009 | Vinegar |
| 2009/0093811 A1 | 4/2009 | Koblish et al. |
| 2009/0112200 A1 | 4/2009 | Eggers |
| 2009/0118729 A1 | 5/2009 | Auth et al. |
| 2009/0118730 A1 | 5/2009 | Mollenauer |
| 2009/0198224 A1 | 8/2009 | McGaffigan |
| 2009/0248002 A1 | 10/2009 | Takashino et al. |
| 2009/0292347 A1 | 11/2009 | Asmus et al. |
| 2009/0306644 A1 | 12/2009 | Mayse et al. |
| 2009/0312753 A1 | 12/2009 | Shadduck |
| 2010/0004650 A1 | 1/2010 | Ormsby et al. |
| 2010/0082022 A1 | 4/2010 | Haley et al. |
| 2010/0152725 A1 | 6/2010 | Pearson et al. |
| 2010/0198216 A1 | 8/2010 | Palanker |
| 2010/0228244 A1 | 9/2010 | Hancock et al. |
| 2010/0268205 A1 | 10/2010 | Manwaring et al. |
| 2010/0268206 A1 | 10/2010 | Manwaring et al. |
| 2010/0268207 A1 | 10/2010 | Manwaring et al. |
| 2010/0268208 A1 | 10/2010 | Manwaring et al. |
| 2010/0268209 A1 | 10/2010 | Manwaring et al. |
| 2010/0268210 A1 | 10/2010 | Manwaring et al. |
| 2010/0268211 A1 | 10/2010 | Manwaring et al. |
| 2010/0268212 A1 | 10/2010 | Manwaring et al. |
| 2010/0268213 A1 | 10/2010 | Manwaring et al. |
| 2010/0268214 A1 | 10/2010 | Manwaring et al. |
| 2010/0268215 A1 | 10/2010 | Manwaring et al. |
| 2010/0268216 A1 | 10/2010 | Manwaring et al. |
| 2010/0268218 A1 | 10/2010 | Ormsby et al. |
| 2011/0004204 A1 | 1/2011 | Dodde et al. |
| 2011/0054456 A1 | 3/2011 | Thompson et al. |
| 2011/0092971 A1 | 4/2011 | Sartor et al. |
| 2011/0152857 A1 | 6/2011 | Ingle |
| 2012/0059367 A1 | 3/2012 | Buysse et al. |
| 2012/0071712 A1 | 3/2012 | Manwaring et al. |
| 2012/0071870 A1* | 3/2012 | Salahieh ............ A61B 5/01 606/33 |
| 2012/0130256 A1 | 5/2012 | Buysse et al. |
| 2012/0150170 A1 | 6/2012 | Buysse et al. |
| 2012/0226270 A1 | 9/2012 | Manwaring et al. |
| 2012/0259323 A1 | 10/2012 | Manwaring et al. |
| 2012/0296326 A1 | 11/2012 | Manwaring et al. |
| 2012/0303026 A1 | 11/2012 | Dycus et al. |
| 2012/0330295 A1 | 12/2012 | Manwaring et al. |
| 2013/0006240 A1 | 1/2013 | McNally et al. |
| 2013/0012934 A1 | 1/2013 | Manwaring et al. |
| 2013/0023866 A1 | 1/2013 | Stringham et al. |
| 2013/0041367 A1 | 2/2013 | Wham et al. |
| 2013/0066310 A1 | 3/2013 | Manwaring et al. |
| 2013/0197502 A1 | 8/2013 | Manwaring et al. |
| 2013/0218152 A1 | 8/2013 | Manwaring et al. |
| 2013/0226165 A1 | 8/2013 | Manwaring et al. |
| 2013/0296838 A1 | 11/2013 | Manwaring et al. |
| 2014/0052119 A1* | 2/2014 | Stewart ............ H05K 13/0046 606/33 |
| 2014/0058381 A1 | 2/2014 | Wham et al. |
| 2014/0058384 A1 | 2/2014 | Buysse et al. |
| 2014/0058385 A1 | 2/2014 | Wham et al. |
| 2014/0074082 A1 | 3/2014 | Denis et al. |
| 2014/0100559 A1 | 4/2014 | Wham et al. |
| 2014/0180266 A1 | 6/2014 | Buysse et al. |
| 2016/0030102 A1 | 2/2016 | Manwaring et al. |
| 2016/0030103 A1 | 2/2016 | Manwaring et al. |
| 2016/0192977 A1 | 7/2016 | Manwaring et al. |
| 2016/0249971 A1 | 9/2016 | Manwaring et al. |
| 2017/0189094 A9 | 7/2017 | Manwaring et al. |
| 2017/0196617 A1 | 7/2017 | Denis et al. |
| 2017/0209200 A1 | 7/2017 | Manwaring et al. |

FOREIGN PATENT DOCUMENTS

| | | |
|---|---|---|
| EP | 2036512 | 3/2009 |
| EP | 2070486 | 6/2009 |
| GB | 2 022 974 | 12/1978 |
| GB | 1 546 624 | 5/1979 |
| JP | 3-51179 B2 | 8/1991 |
| JP | 2558584 B2 | 11/1996 |
| JP | 10-277050 A | 10/1998 |
| RU | 2 072 118 C1 | 1/1997 |
| WO | WO-82/00746 | 3/1982 |
| WO | WO 92/017121 | 10/1992 |
| WO | WO-93/021839 | 11/1993 |
| WO | WO1994/08524 * | 4/1994 |
| WO | WO-96/026677 | 11/1996 |
| WO | WO 9937227 A1 | 7/1999 |
| WO | WO-01/006943 | 2/2001 |
| WO | WO-04/014217 | 2/2004 |
| WO | WO-04/076146 | 9/2004 |

(56) References Cited

FOREIGN PATENT DOCUMENTS

| WO | WO-06/017517 | 2/2006 |
|---|---|---|
| WO | WO-06/029649 | 3/2006 |
| WO | WO 2007080578 A2 | 7/2007 |
| WO | WO-08/060668 | 5/2008 |

OTHER PUBLICATIONS

Metcal Soldering Iron Catalog—2006.
URSI EMTS 2004, pp. 489-491, *Electromagnetic Probes for Living Tissue Cauterization*.
"High Temp Metals." NI2001201 Technical Data. High Temp Metals, Inc., n.d. Web. Jul. 13, 2012. <http://www.hightempmetals.com/techdatafnitempNi200data.php.
International Preliminary Report on Patentability from related PCT Patent Application No. PCT/US2010/031114, dated Nov. 1, 2011.
International Preliminary Report on Patentability from related PCT Patent Application No. PCT/US2010/031114, dated Jan. 21, 2011.
International Preliminary Report on Patentability from related PCT Patent Application No. PCT/US2011/050417, dated Apr. 12, 2012.
International Preliminary Report on Patentability from related PCT Patent Application No. PCT/US2012/032656, dated Oct. 23, 2012.
International Preliminary Report on Patentability from related PCT Patent Application No. PCT/US2012/032659, dated Nov. 23, 2012.
International Preliminary Report on Patentability from related PCT Patent Application No. PCT/US2012/038005, dated Nov. 23, 2012.
International Preliminary Report on Patentability from related PCT Patent Application No. PCT/US2012/055229, dated Feb. 1, 2013.
Written Opinion of the International Preliminary Examining Authority from related PCT Patent Application No. PCT/US2011/050417, dated Feb. 6, 2013.
International Preliminary Report on Patentability from related PCT Patent Application No. PCT/US2012/068027, dated Feb. 25, 2013.
Visioli, Antonio. Practice PID Control: London: Springer-Verlag, Jan. 18, 2006. Print.
International Search Report and Written Opinion from related PCT Application US2012/032661, dated Aug. 19, 2013.
International Search Report and Written Opinion from related PCT Application US2012/032659, dated Oct. 8, 2013.
International Search Report and Written Opinion from related PCT Application US2012/032565, dated Oct. 8, 2013.
International Preliminary Report on Patentability from related PCT Application US2012/038005, dated Nov. 19, 2013.
International Preliminary Report on Patentability from related PCT Application US2012/068027, dated Jun. 19, 2014.
Translation of Office Action from related Japanese Patent Application No. 2012-506188, PCT US2010-031114.
European Search Report from European Application No. 12865504.0-1652, dated Nov. 28, 2014.
Supplemental European Search Report from European Patent Application No. EP 12767458 dated Jan. 30, 2015.
Denis et al., "System and Method of Controlling Power Delivery to an Electrosurgical Instrument," U.S. Appl. No. 61/669,671, filed Jul. 10, 2012, 59 pages.
Denis et al., "Thermal Surgical Tool," U.S. Appl. No. 61/567,603, filed Dec. 6, 2011, 33 pages.
Extended European Search Report, dated Nov. 10, 2016, for European Application No. 10765134.1-1659, 8 pages.
International Preliminary Report on Patentability, dated Oct. 8, 2013, for International Application No. PCT/US2012/032661, 8 pages.
International Search Report and Written Opinion, dated Feb. 1, 2013, for International Application No. PCT/US2012/055229, 11 pages.
International Search Report and Written Opinion, dated Feb. 15, 2013, for International Application No. PCT/US2012/068027, 8 pages.
International Search Report and Written Opinion, dated Jan. 21, 2011, for International Application No. PCT/US2010/031114, 12 pages.
International Search Report and Written Opinion, dated Nov. 23, 2012, for International Application No. PCT/US2012/038005, 9 pages.
International Search Report and Written Opinion, dated Oct. 23, 2012, for International Application No. PCT/US2012/032656, 13 pages.
Manwaring et al., "Adjustable Ferromagnetic Coated Conductor Thermal Surgical Tool," U.S. Appl. No. 61/170,203, filed Apr. 17, 2009, 36 pages.
Manwaring et al., "Surgical Multi-Mode Tool With Ferromagnetic Coated Conductor for Adjustable Thermal Energy Delivery," U.S. Appl. No. 61/170,207, filed Apr. 17, 2009, 43 pages.
Manwaring et al., "Thermally Adjustable Surgical or Therapeutic Tool and Method of Use," U.S. Appl. No. 61/170,220, filed Apr. 17, 2009, 41 pages.

* cited by examiner

PLANAR FERROMAGNETIC COATED SURGICAL TIP AND METHOD FOR MAKING

BACKGROUND OF THE INVENTION

1. The Field of the Invention

The present invention relates to surgical tools. More specifically, the present invention relates to an improved ferromagnetic surgical tips and method of making such surgical tips.

2. State of the Art

Surgery generally involves cutting or dissection of tissue or other materials. These applications are generally performed by cutting tissue, fusing tissue, or tissue destruction. Current electrosurgery modalities used for cutting, coagulating, desiccating, ablating, or fulgurating tissue, have undesirable side effects and drawbacks. Although recent innovations have provided ferromagnetic coated tungsten cutting instruments, such instruments have some limitations. For example, surgical tips having tungsten wire substrates have limited malleability because the tungsten substrate is very stiff. In addition, tungsten wire can be difficult to plate with other materials, requiring special plating processes and attention to quality control. Differences in the coefficient of thermal expansion between tungsten and ferromagnetic coatings may also cause cumulative stresses over time between the layers when the parts heat up and cool down. Furthermore, the stiffness of tungsten wire limits its malleability when forming customized shapes. Tungsten is also a relatively rare and expensive metal. The high cost, combined with the difficulty and cost associated with bending and plating it, make such tungsten wire heating elements comparatively expensive and difficult to use.

SUMMARY OF THE INVENTION

The present invention relates to improved structures for manufacturing surgical tips. In one aspect, the present invention provides a metal sheet comprising a plurality of surgical dissection tip substrates connected at the base of the surgical dissection tip substrate by a tab, wherein each surgical dissection tip substrate comprises two substantially parallel planar extension strips connected to a tip.

In some embodiments, the surgical dissention tip may be configured in a planar spatula shape having a greater cross sectional area than the thickness of the substrate.

The present invention also provides improved surgical tips having ferromagnetic coatings and methods for manufacturing such surgical tips.

In some embodiments, the present invention provides a surgical dissection tip, comprising a substrate comprising beryllium copper; and a ferromagnetic layer coating at least a portion of the substrate. In other embodiments, the substrate may comprise other alloys of copper, tungsten alloys, cobalt-based alloys, or nickel-based alloys. It is also contemplated that the substrate of the present invention may comprise clad materials, such as copper clad beryllium copper, copper clad stainless steel, copper clad titanium, and copper clad Haynes 25.

In some embodiments, the beryllium copper may comprise greater than 1 percent by weight beryllium. In other embodiments, the beryllium copper comprises greater than 1.5 percent by weight beryllium. In yet other embodiments, the beryllium copper comprises about 2 percent by weight beryllium.

In other embodiments, the substrate comprises beryllium copper laminated to one or more layer of copper. In other embodiments, the substrate comprises beryllium copper laminated between two layers of copper. In these cases, the sandwich can be optimized with a wide variety of materials to achieve the appropriate balance of thermal conductivity, stiffness and electrical conductivity.

In some embodiments, the ferromagnetic coating is a ferromagnetic alloy. In some embodiments, the ferromagnetic coating comprises a material selected from the group consisting of a nickel/iron alloy and a nickel/chromium alloy. In some embodiments, the ferromagnetic coating may comprise a nickel iron alloy having about 50-80% by weight nickel and 50-20% by weight iron.

In another aspect, the present invention provides a surgical dissection tip, comprising: a substrate comprising beryllium copper, wherein the substrate comprises a planar tip having two planar extension strips, wherein the planar tip and the planar extension strips are within the same plane; and a ferromagnetic layer coating at least a portion of the planar tip.

In some embodiments, the two planar extension strips are substantially parallel.

In other embodiments, the planar extension strips have a width in the plane of the extension strips and a thickness in a plane perpendicular to the plane of the extension strips, wherein the width of each extension strip is greater than the thickness of the extension strip.

In another aspect, the present invention provides a method for manufacturing a surgical dissection tip, comprising: forming a substrate comprising beryllium copper, wherein the substrate comprises a planar tip having two planar strips extending from the tip, wherein the tip and the planar extension strips are within the same plane; and coating at least a portion of the tip of the substrate with a ferromagnetic layer.

In some embodiments, the two planar extension strips are substantially parallel.

In some embodiments, the substrate comprising beryllium copper is formed by a process comprising electrodeposition.

In some embodiments, the thickness of the planar sheet is from about 0.3 mm to about 1.5 mm.

In another aspect, the present invention provides a method for manufacturing a surgical dissection tip, comprising: providing a planar sheet of substrate material comprising beryllium copper; removing material from the sheet of substrate to provide a planar tip having two planar strips extending from the tip, wherein the tip and the planar extension strips are within the same plane; and coating at least a portion of the tip of the substrate with a ferromagnetic layer.

In some embodiments, the two planar extension strips are substantially parallel.

In some embodiments, the material from the sheet of substrate is removed by a process comprising etching.

In some embodiments, the material from the sheet of substrate is removed by a process comprising cutting. Alternatively, the material from the sheet of substrate may be removed by such processes as stamping, laser etching, laser cutting, and the like.

In other embodiments, the planar tip has a central region and an edge and the thickness of the central region is greater than the thickness at the edge to provide a sharper edge for cutting.

In yet other embodiments, the thickness of the planar sheet is from about 0.3 mm to about 1.5 mm.

These and other aspects of the present invention are realized in a thermally adjustable surgical tool as shown and described in the following figures and related description.

BRIEF DESCRIPTION OF THE DRAWINGS

Various embodiments of the present invention are shown and described in reference to the numbered drawings wherein.

It will be appreciated that the drawings are illustrative and not limiting of the scope of the invention which is defined by the appended claims. The embodiments shown accomplish various aspects and objects of the invention. It is appreciated that it is not possible to clearly show each element and aspect of the invention in a single figure, and as such, multiple figures are presented to separately illustrate the various details of the invention in greater clarity. Similarly, not every embodiment need accomplish all advantages of the present invention.

DETAILED DESCRIPTION

The invention and accompanying drawings will now be discussed in reference to the numerals provided therein so as to enable one skilled in the art to practice the present invention. The drawings and descriptions are exemplary of various aspects of the invention and are not intended to narrow the scope of the appended claims.

As used herein, the term "ferromagnetic," "ferromagnet," and "ferromagnetism" refers to any ferromagnetic-like material that is capable of producing heat via magnetic induction, including but not limited to ferromagnets and ferrimagnets.

Figure 1A:
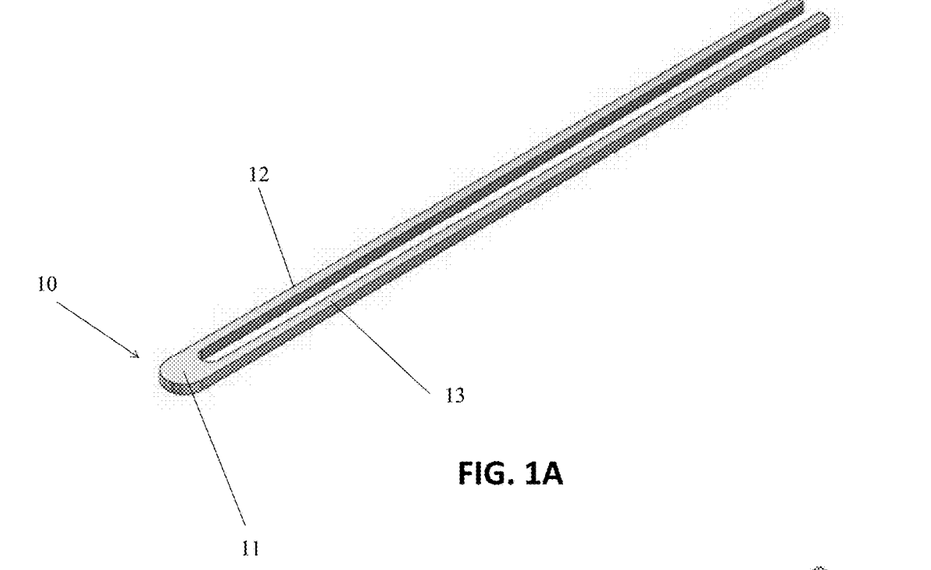
FIG. 1A shows a flat thermal surgical heating element.
Figure 1B:
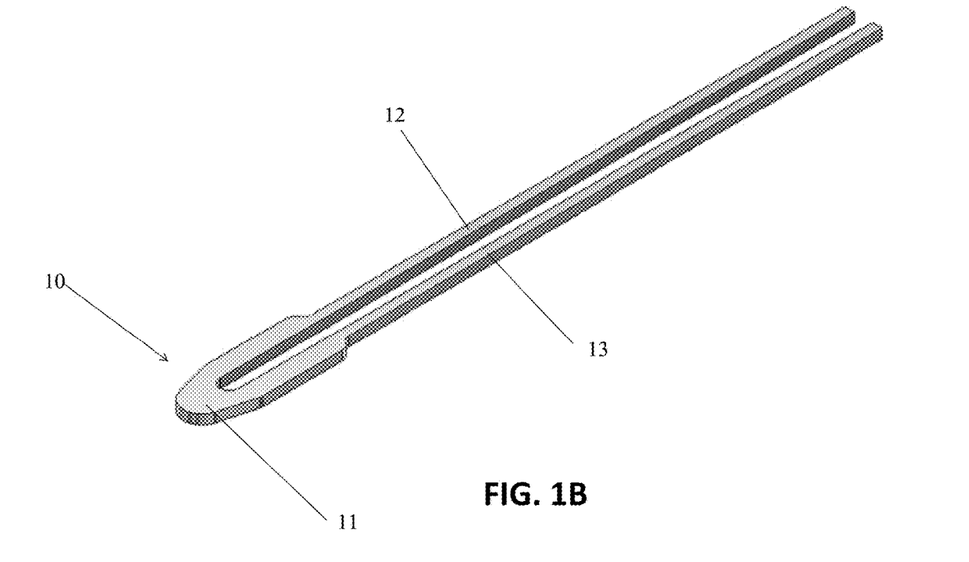
FIG. 1B shows a flat thermal surgical heating element with a wider tip.
Figure 1C:
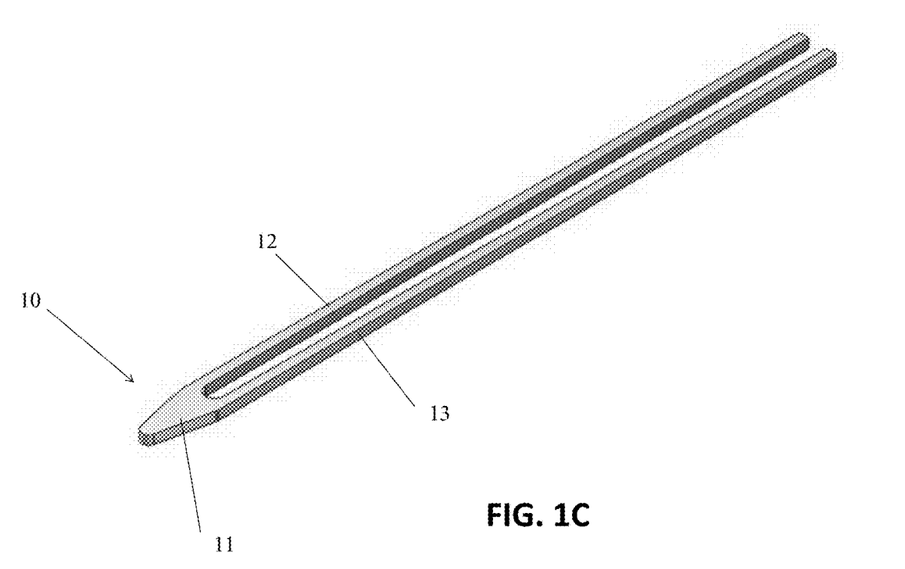
FIG. 1C shows a flat thermal surgical heating element having a pointed tip.
Figure 1D:
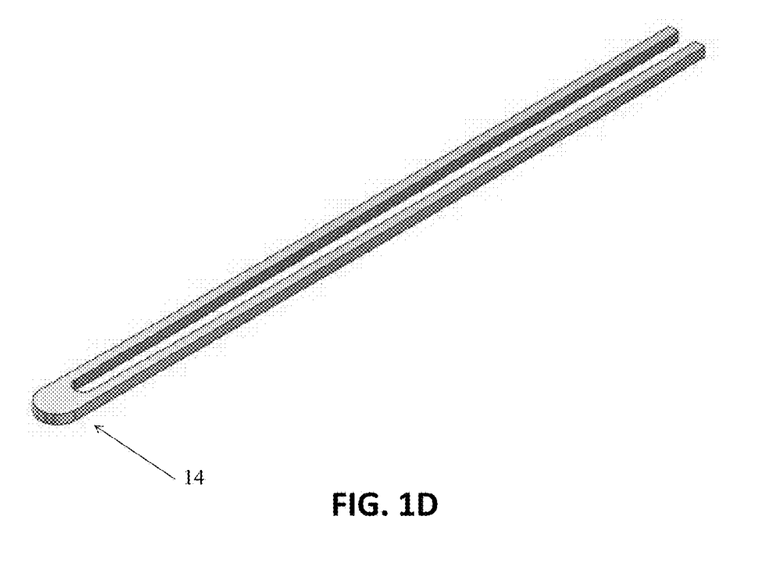
FIG. 1D shows a flat thermal surgical heating element having a tip coated with a ferromagnetic material.
Figure 1E:
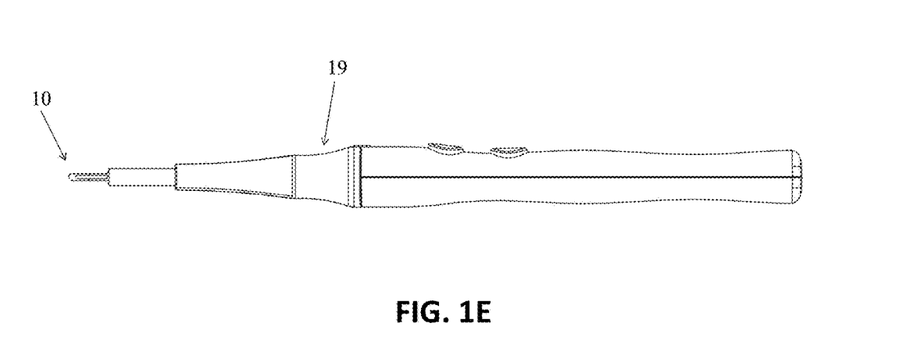
FIG. 1E shows a surgical instrument having an exemplary surgical tip.

FIGS. 1A, 1B, 1C and 1C, show perspective views of several embodiments of the surgical tip of the present invention. FIGS. 1A, 1B, 1C each show a surgical tip substrate 10 comprising a planar tip 11 having two substantially parallel planar strips 12 and 13 extending from the tip 11, wherein the tip 11 and the planar extension strips 12 and 13 are within the same plane. FIGS. 1A, 1B and 1C further show the shape of a spatula area wherein the width of the spatula is greater than the thickness of the substrate. FIG. 1D shows a surgical tip substrate 10 having a coating 14 on at least a portion of the tip 11 of the substrate, wherein the coating comprises a ferromagnetic layer. FIG. 1E shows a surgical tool 19 having exemplary surgical tip 10.

Figure 2A:
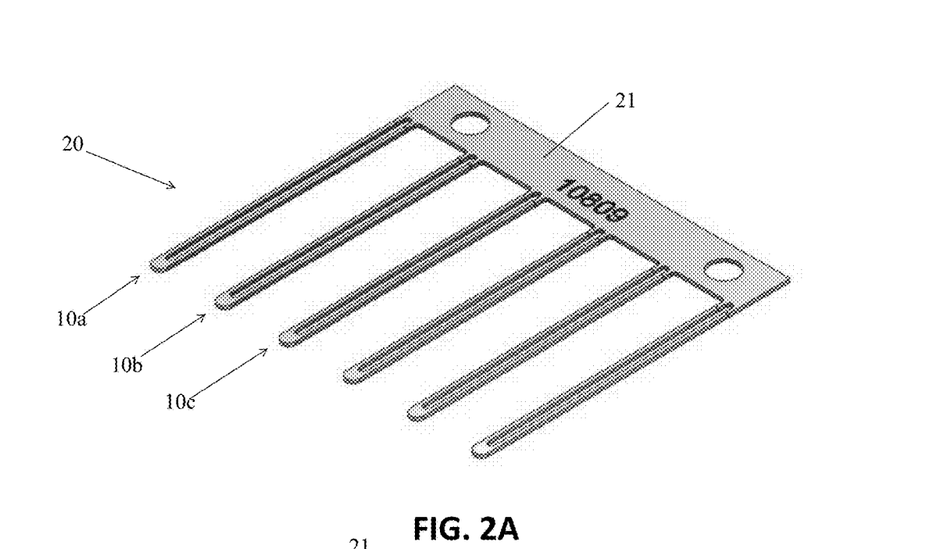
FIG. 2A shows a perspective view of multiple thermal surgical heating elements that are manufactured from a single sheet of material.
Figure 2B:
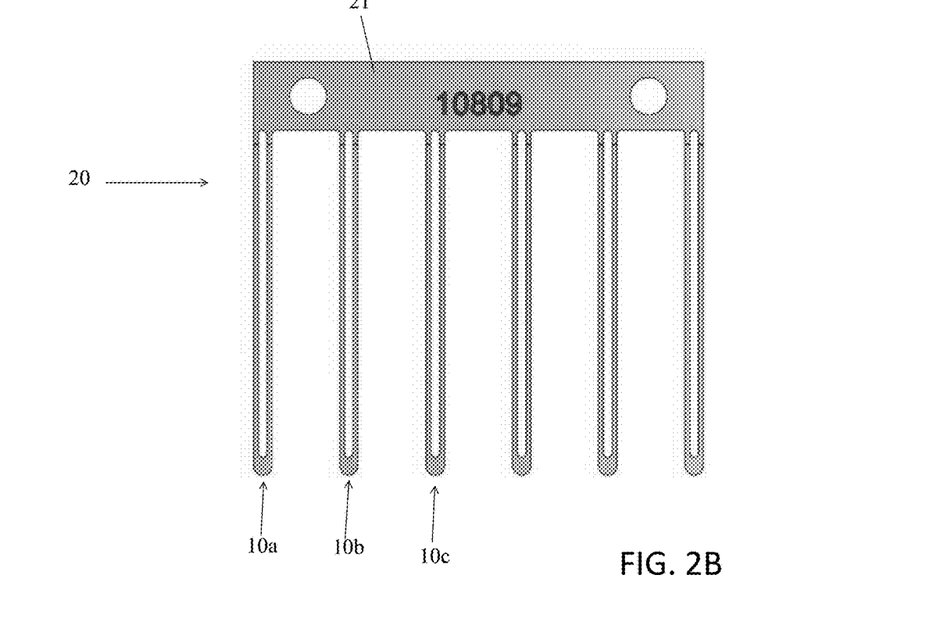
FIG. 2B shows a top view of multiple thermal surgical heating elements that are manufactured from a single sheet of material.

Turning to FIGS. 2A and 2B, there is shown a series of surgical tip substrates 10a, 10b and 10c, manufactured together as a single unit and connected via a tab 21 from which each of the individual surgical tip substrates 10a, 10b, and 10c extend. The surgical tip substrates 10a, 10b, and 10c are eventually separated from the tab 21 to form individual surgical tips that will be installed in a thermal surgical tool.

Figure 3A:
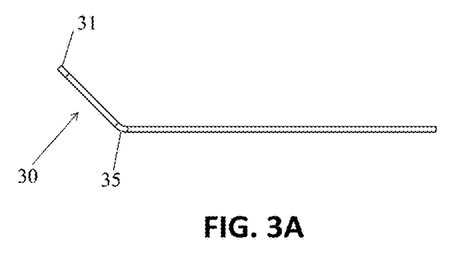
FIG. 3A shows a side view of a bent surgical tip.
Figure 3B:
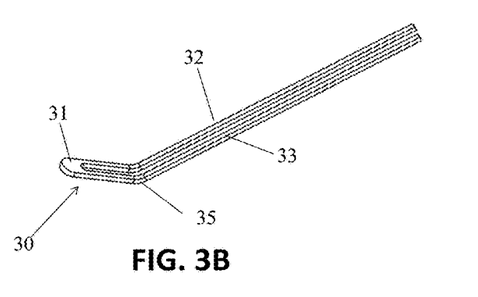
FIG. 3B shows a perspective view of a bent surgical tip.

FIGS. 3A and 3B illustrate an embodiment in which the flat surgical tip substrate is bent, so as to provide a surgical tip configuration that can be used to dissect tissue in locations or at angles that may be too difficult for a straight surgical tip.

As shown in FIGS. 3A and 3B, one particular embodiment of the invention is shown, wherein a surgical tip substrate 30 has surgical tip 31 with planar extensions 32 and 33, each of which have a bend 35. The bend 35 can be made either as part of the manufacturing process (after the flat surgical tip structure has been created) or by the end user. The location of the bend is selected at a location along the extensions that facilitates a bent tip size suitable for the particular surgical technique being employed by the surgeon.

Figure 4A:
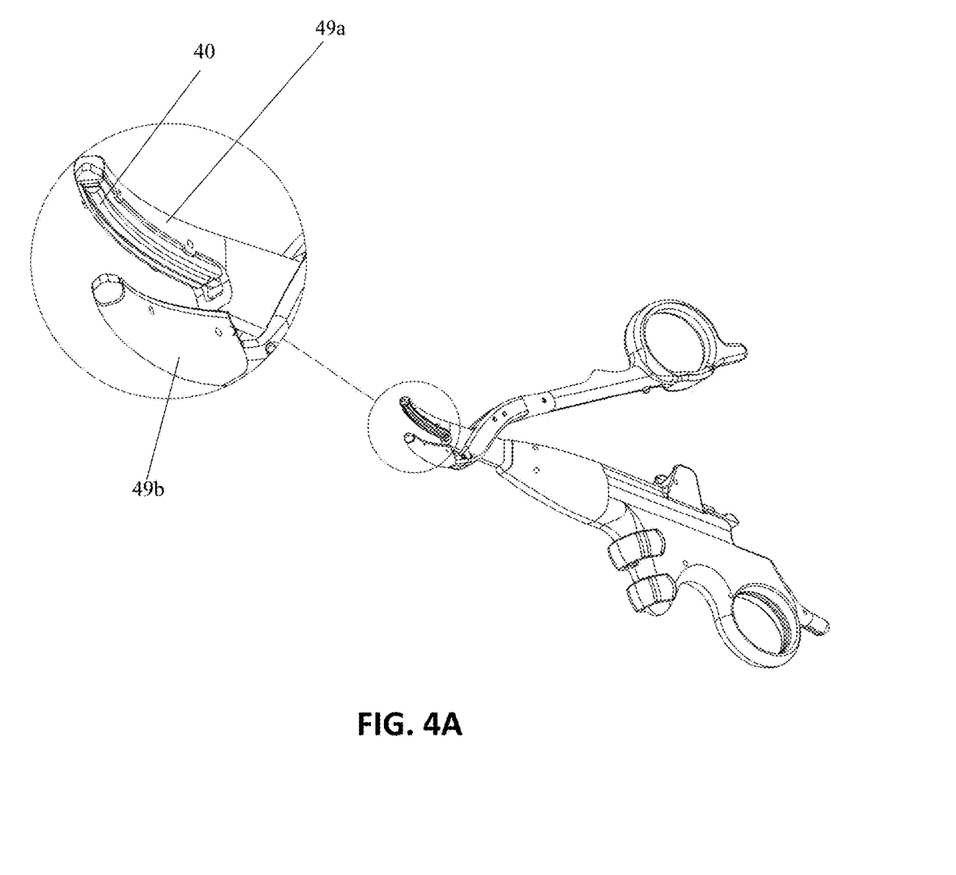
FIG. 4A shows shears, with a detail view of the shears tip.
Figure 4B:
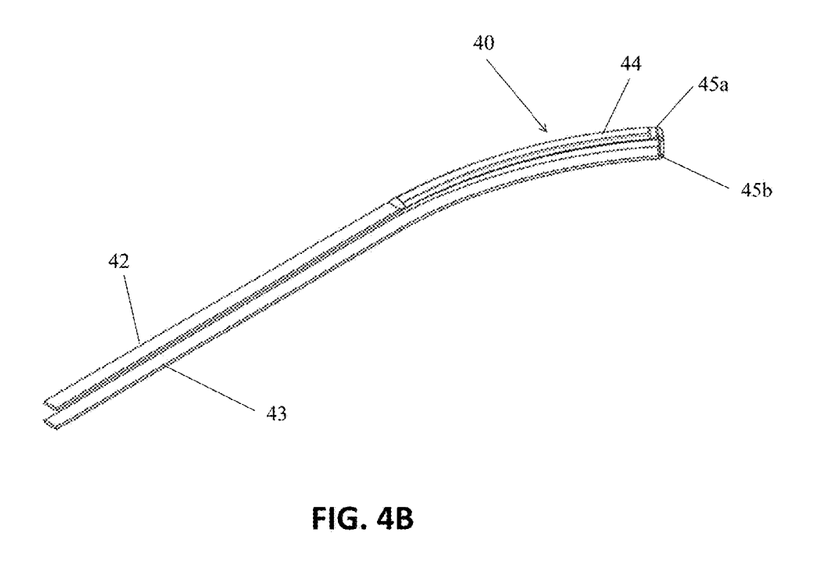
FIG. 4B shows a perspective view of a shears heating element.
Figure 4C:
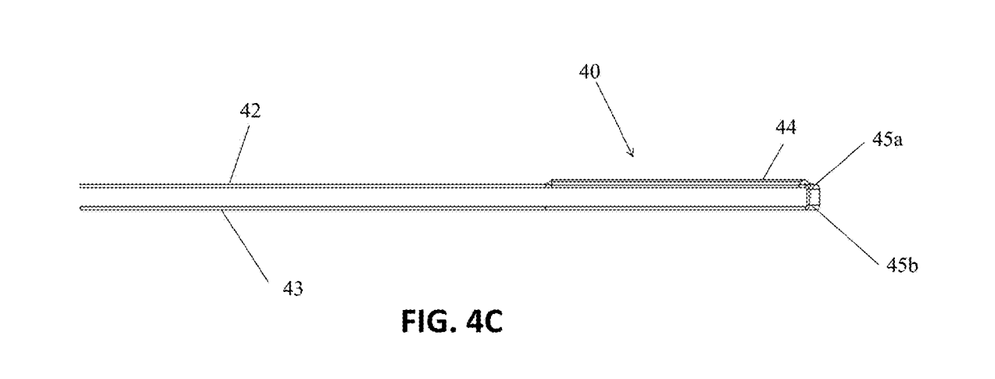
FIG. 4C shows a side view of a shears heating element.

FIGS. 4A, 4B and 4C provide various views of a set of surgical shears (FIG. 4A) and the heating elements (FIGS. 4B and 4C) used in such shears. The surgical shears shown in FIG. 4A include surgical tip substrate 40 on at least one of the opposing blades 49a and 49b.

As shown in more detail in FIGS. 4B and 4C, in one particular embodiment of the invention the surgical tip substrate 40 used in such surgical shears comprises extensions 42 and 43 extending from the proximal end where bends 45a and 45b are located. In this particular example, the surgical tip may be manufactured by creating a long planar strip. The location of the bends 45a and 45b may be pre-determined by manufacturing the strip with score marks, peforations, thinner material, stamped depressions, or the like, at the location of the bends, so as to facilitate customized bending the substrate by the end user surgeon. The long planar strip is then bent at the location of the score marks or, in the absence of score marks, at any location where a bend is desired. The surgical tip is coated with a ferromagnetic material, either prior to the bending step or following the bending step. Coating the surgical tip with a ferromagnetic material following the bending step would, of course, have the advantage of avoid possible stress fractures in the ferromagnetic material during the bending process.

As further shown in FIGS. 4A, 4B and 4C, the surgical tip may further include a raised portion 44 so as to create an area of greater pressure at the apex of the raised portion 44 when the shears are clamped down on tissue, thereby cutting the tissue. The raised portion 44 can be created either by depositing additional beryllium copper material or other metal alloy material to the planar substrate, or by depositing a larger quantity of ferromagnetic material on the flat beryllium copper substrate, or other metal alloy substrate, when the ferromagnetic coating is applied.

Figure 5A:
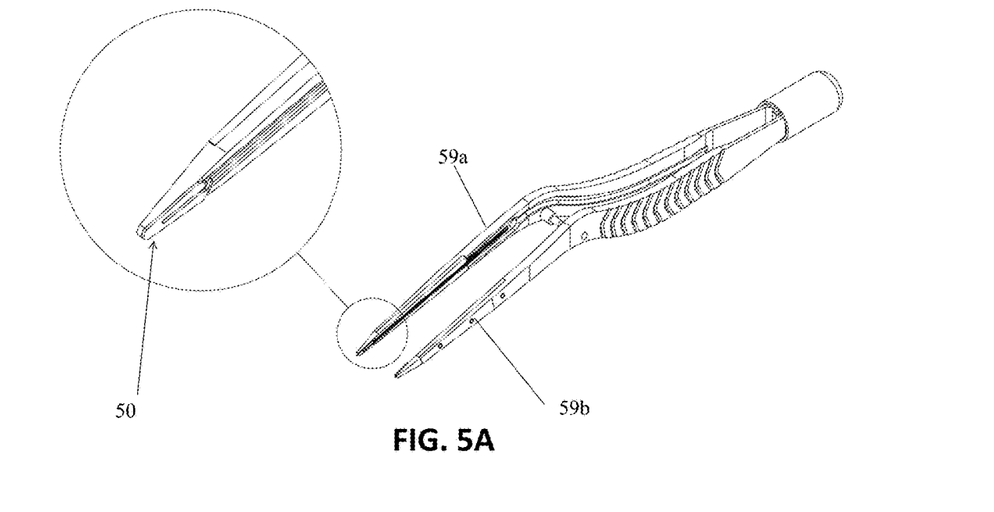
FIG. 5A shows forceps, with a detail view of the forceps blade.
Figure 5B:
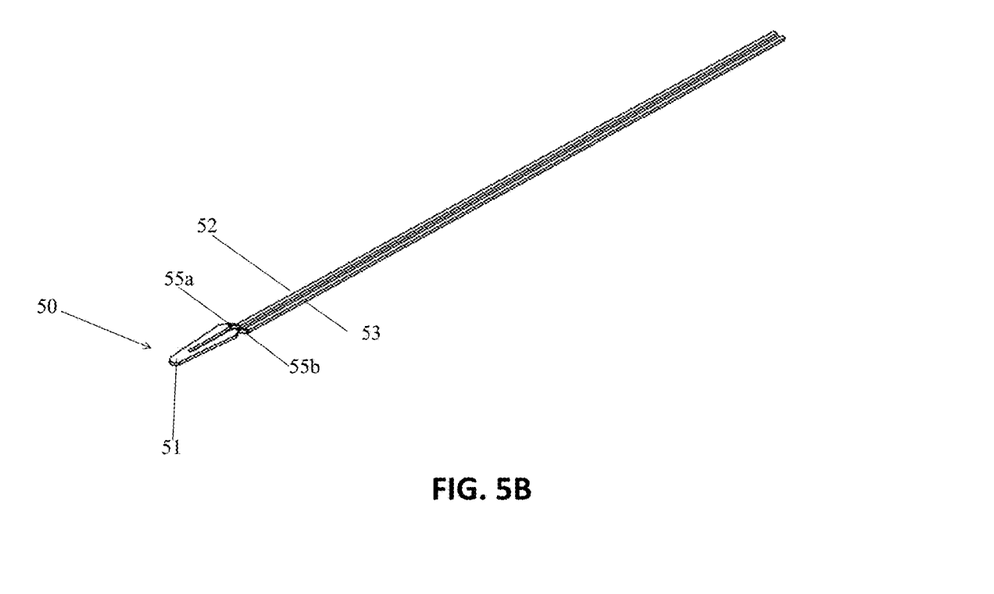
FIG. 5B shoes a forceps heating element.

FIGS. 5A and 5B illustrate another embodiment of the invention, wherein the surgical tip 50 is applied to forceps comprising forcep tips 59a and 59b. The surgical tip 50 may be used on one or both sides of the forcep ends 59a and 59b. The construction of the surgical tip 50. In this particular example, the surgical tip may be manufactured by creating a long planar strip have two extensions 52 and 53 that extend from the top portion 51. The location of the bends 55a and 55b may be pre-determined by manufacturing the strip with score marks at the location of the bends. The long planar strip is then bent at the location of the score marks or, in the absence of score marks, at any location where a bend is desired so as to conform to the shape of the forcep tip. The surgical tip is coated with a ferromagnetic material, either prior to the bending step or following the bending step. Coating the surgical tip with a ferromagnetic material following the bending step would, of course, have the advantage of avoid possible stress fractures in the ferromagnetic material during the bending process.

As will be discussed in additional detail below, the surgical tip preferably uses a ferromagnetic coated conductor to treat or destroy tissue (i.e. endothelial tissue welding, homeostasis, ablation, etc). It will be appreciated that the surgical tip may use heat to incise tissue and not cut tissue in the sense of a sharp edge being drawn across the tissue as with a conventional scalpel. While the embodiments of the present invention could be made with a relatively sharp edge so as to form a cutting blade, such is not necessary as the heated coating discussed herein will separate tissue without the need for a cutting blade or sharp edge. However, for convenience, the term cutting is used when discussing separating or dissecting tissue.

In the various embodiments of the surgical tips described herein, a control mechanism, such as a foot pedal may be used to control output energy produced by a power subsystem. The energy from the power subsystem may be sent via radio frequency (RF) or oscillating electrical energy along a cable to a handheld surgical tool, which contains substrate 10 having at least a section thereof circumferentially coated with a ferromagnetic coating 14. The ferromagnetic coating 14 may convert the electrical energy into available thermal energy via induction and corresponding hysteresis losses in the ferromagnetic material disposed around the conductor substrate 10.

Application of a magnetic field (or magnetizing) to the ferromagnetic coating may produce an open loop B-H curve (also known as an open hysteresis loop), resulting in hysteresis losses and the resultant thermal energy. Electrodeposited films, such as a nickel-iron coating like PERMALLOY™, may form an array of randomly aligned microcrystals, resulting in randomly aligned domains, which together may have an open loop hysteresis curve when a high frequency current is passed through the conductor. The alternating RF current in the conductor's surface produces an alternating magnetic field, which may excite the domains in the ferromagnetic coating 14. As the domains realign with each oscillation of the current, hysteresis losses in the coating may cause inductive heating. Thus, heating occurs due to a combination of hysteresis losses and resistive heating due to the skin effect.

The RF energy may travel along the conductor's surface in a manner known as the "skin effect". The current is forced through the narrow cross-sectional area of the ferromagnetic plating resulting in a high current density and therefore joule heating.

The RF conductor from the signal source up to and including the tip, may form a resonant circuit at a specific frequency (also known as a tuned circuit). Changes in the tip "detune" the circuit. Thus, should the ferromagnetic coating 14 or the conductor substrate 10 become damaged, the circuit may likely become detuned. This detuning may reduce the efficiency of the heating of the ferromagnetic coating 14 such that the temperature will be substantially reduced. The reduced temperature may ensure little or no tissue damage after breakage.

It should be understood that the handheld surgical tool may include indicia of the power being applied and may even include a mechanism for controlling the power. Thus, for example, a series of lights could be used to indicate power level, or the handheld surgical tool could include a switch, rotary dial, set of buttons, touchpad or slide that communicates with the power source to regulate power and thereby affect the temperature at the ferromagnetic coating 14 to having varying effects on tissue. Examples of such surgical tools are shown in U.S. Pat. No. 8,425,503. While the controls may be present on the foot pedal or the handheld surgical tool, they may also be included in the power subsystem or even a separate control instrument. Safety features such as a button or touchpad that must be contacted to power the handheld surgical tool may be employed, and may include a dead man's switch.

While the ferromagnetic coating 14 heats through the mechanisms of skin effect and joule heating, it also provides a temperature cap due to its Curie temperature, which causes the temperature of the ferromagnetic material to stabilize around the Curie temperature if sufficient power is provided to reach the Curie temperature. Once the temperature has dropped below the Curie temperature, the material again heats up to the Curie temperature. Thus, the temperature in the ferromagnetic coating may reach the Curie temperature with the application of sufficient power, but will not likely exceed the Curie temperature.

The surgical tip 10 allows the power output to be adjustable in order to adjust the temperature of the tool and its effect on tissue. This adjustability gives the surgeon precise control over the effects that may be achieved by the handheld surgical tool. Tissue effects such as cutting, hemostasis, tissue welding, tissue vaporization and tissue carbonization occur at different temperatures. By using a foot pedal (or some other user control) to adjust the power output, the surgeon (or other physician, etc.) can adjust the power delivered to the ferromagnetic coating 14 and consequently control the tissue effects to achieve a desired result.

Thermal power delivery can be controlled by varying the amplitude, frequency or duty cycle of the alternating current waveform, or alteration of the circuit to effect the standing wave driving the ferromagnetic coated conductor, which may be achieved by input received by the foot pedal, the power subsystem, or the controls on the handheld surgical tool.

One additional advantage achieved by the use of a ferromagnetic material is that the ferromagnetic material can be heated to a cutting temperature in a brief interval of time (typically as short one quarter of a second). Additionally, because of the relatively low mass of the coating, the small thermal mass of the conductor, and the localization of the heating to a small region due to construction of the handheld surgical tool, the material will also cool extremely rapidly. This provides a surgeon with a precise thermal tool while reducing accidental tissue damage caused by touching tissue when the thermal tool is not activated.

It will be appreciated that the time period required to heat and cool the handheld surgical tool will depend, in part, on the relative dimensions of the conductor substrate 10 and the ferromagnetic coating 14 and the heat capacity of the structure of the surgical tool, as well as its heat capacity and thermal conductivity. For example, the desired time periods for heating and cooling of the handheld surgical tool can be minimized with a beryllium copper conductor substrate having a thickness of from about 0.2 to about 0.5 mm, e.g. about 0.375 mm, and a ferromagnetic coating of a Nickel Iron alloy (such as NIRON™ available from Enthone, Inc.

of West Haven, Conn.) about the conductor substrate. In some embodiments, the thickness of the ferromagnetic coating may be between about 0.05 µm and about 500 µm. In some embodiments, the thickness of the ferromagnetic coating may be between about 1 µm and about 50 µm. Different lengths of the conductor substrate may be coated depending on desired use, such as two centimeter long coating when used as a cutting tool.

One advantage of the present invention is that a sharp edge is not needed. When power is not being supplied to the surgical tool, the tool will not inadvertently cut tissue of the patient or of the surgeon if it is dropped or mishandled. If power is not being supplied to the conductor substrate 10 and coating 14, the "cutting" portion of the tool may be touched without risk of injury. This is in sharp contrast to a cutting blade which may injure the patient or the surgeon if mishandled.

Other additions may also be placed on the handpiece in various locations. This may include a sensor to report temperature or a light to illuminate the surgical area.

This surgical tips described herein may provide advantages over monopolar and bipolar electrical systems currently available because the thermal damage may remain very close to the ferromagnetic surface of the coated region, whereas monopolar and bipolar electrical tissue ablation may frequently cause tissue damage for a distance away from the point of contact. This method may also overcome disadvantages of other thermal devices based upon resistive heating, which may require more time to heat and cool, and thus present greater patient risk.

Furthermore, the thin ferromagnetic coating 14, disposed along a small segment of the conductor, may reduce the heating of other non-target material in the body, such as blood when working within the heart in atrial ablation—which can lead to complications if a clot is formed. The small thermal mass of the conductor substrate 10, and localization of the heating to a small region provided by the construction of the tool (i.e. ferromagnetic coating 14 and adjacent structures) provides a reduced thermal path for heat transfer in directions away from the location of the ferromagnetic coating 14. This reduced thermal path may result in the precise application of heat at only the point desired. As this technology alone does not employ a spark or an arc like monopolar or bipolar technology, risks of ignition, such as by anesthetic gasses within or around the patient by sparks, are also reduced.

The thermal surgical tip 10 may be used for a variety of therapeutic means—including sealing, "cutting" or separating tissue, coagulation, or vaporization of tissue. In one configuration, the thermal surgical tip 10 may be used like a knife or sealer, wherein the surgeon is actively "cutting" or sealing tissue by movement of the ferromagnetic coating 14 through tissue. The thermal action of the embodiments disclosed here may have distinct advantages including substantial reduction, if not elimination, of deep tissue effects compared with those associated with monopolar and bipolar RF energy devices.

In another configuration, the ferromagnetic coated substrate 10 may be inserted into a lesion and set to a specific power delivery or variable power delivery based on monitored temperature. The thermal effects on the lesion and surrounding tissue may be monitored until the desired thermal effect is achieved or undesired effects are noticed. One advantage of the application of the ferromagnetic coated conductor is that it may be cost-effective compared to microwave or thermal laser modalities and avoids the undesired tissue effects of microwave lesion destruction. Thus, for example, a surgeon can insert the ferromagnetic coated conductor into a tumor or other tissue to be destroyed and precisely control the tissue damage that is created by activating the handheld surgical tool.

Dynamic load issues can be caused by the interaction of the ferromagnetic coated substrate 10 with various tissues. These issues may be minimized by the standing current wave being maximized at the load location. Multiple different frequencies can be used, including frequencies from 4 megahertz to 24 gigahertz, or between 12 MHz and 200 MHz. In some regulated countries it may be preferable choose frequencies in the ISM bands such as bands with the center frequencies of 6.78 MHz, 13.56 MHz, 27.12 MHz, 40.68 MHz, 433.92 MHz, 915 MHz, 2.45 GHz, 5.80 GHz, 24.125 GHz, 61.25 GHz, 122.5 GHz, 245 GHz. In one embodiment, the oscillator uses an ISM Band frequency of 40.68 MHz, a class E amplifier, and a length of coaxial cable, all of which may be optimized for power delivery to a ferromagnetic coated substrate 10 with a ferromagnetic coating 14 consisting of a thickness of between 0.05 micrometer and 500 micrometers, and preferably between 1 micrometer and 50 micrometers, with the optimal plating thickness being five skin depths at the excitation frequency. A useful estimate may be to start the ferromagnetic coating thickness at 10% of the conductor diameter or thickness, and up to 5 mm long. However, the ferromagnetic coating may be disposed as far along the length or along multiple regions of the conductor as where heating may be desired. (The ferromagnetic coating 14 may be formed from a Nickel Iron (NiFe) alloy, such as NIRON™ from Enthone, Inc. of West Haven, Conn., or other ferromagnetic coatings, including Co, Fe, $FeOFe_2O_3$, $NiOFe_2O_3$, $CuOFe_2O_3$, $MgOFe_2O_3$, MnBi, Ni, MnSb, $MnOFe_2O_3$, $Y_3Fe_5O_{12}$, $CrO_2$, MnAs, EuO, magnetite, yttrium iron garnet, and PERMALLOY™.) The size of the conductor, size of the ferromagnetic coating, associated thicknesses, shape, primary geometry, composition, power supply and other attributes may be selected based on the type of procedure and surgeon preferences. For example, a brain surgeon may desire a small instrument in light handheld package designed for quick application within the brain, while an orthopedic surgeon may require a larger device with more available power for operation on muscle.

Copper Beryllium Alloys

The conductor substrate 10 may be formed from any one of various copper beryllium alloys, or combinations of copper beryllium alloy with additional layers of copper. Copper beryllium alloys generally fall into two categories: alloys having high strength, and alloys having high conductivity. In some embodiments of the present invention, the copper beryllium alloys are selected from the group of alloys having high strength, such as Alloys 25, 190, 290, M25 and 165. Such alloys generally comprise a beryllium content ranging from about 1.5 to about 2.0 percent by weight, with the balance comprising copper. For example, Alloys 25, 190 and 290 (designated as Copper Alloy UNS No. C17200) comprise beryllium ranging from 1.8 to 2.0% by weight, a minimum of 0.2 percent by weight cobalt+nickel, a maximum of 0.6 percent cobalt+nickel+iron and a maximum of 0.02 percent lead. Suitable beryllium copper alloys may be obtained from numerous commercially available sources, such as Materion Corporation (Elmore Ohio).

In one aspect of the present invention, the beryllium copper alloy contemplated is Alloy 25, which attains a high strength and hardness, with a tensile strength exceeding 200 ksi, and a hardness approaching Rockwell C45. Alloy 25 also exhibits exceptional resistance to stress relaxation at elevated temperatures, making it particularly useful in thermal surgical applications.

In other embodiments, the substrate may comprise other alloys of copper, such as brass or phosphor bronze.

In other embodiments, the substrate may comprise titanium. In other embodiments, the substrate may comprise tungsten alloys, such as Tungsten molybdenum or tungsten rhenium. In yet other embodiments, the substrate may comprise such as cobalt-based alloys, for example, Haynes 25/L605 or Haynes 188. In yet other embodiments, the substrate may comprise nickel-based alloys, such as Inconel, Hastelloy, Nimonic, or Rene41. It is also contemplated that the substrate of the present invention may comprise clad materials, such as copper clad berrylium copper, copper clad stainless steel, copper clad titanium, and copper clad Haynes 25.

Alternative Substrate Configurations

In addition, the conductor substrate 10 may also comprise a multi-layered laminate comprising beryllium copper or other metal or metal alloy laminated with one or more layers of copper. In some embodiments, the present invention contemplates a conductor substrate comprising a core layer of beryllium copper laminated between two layers of copper.

In other embodiments, the present invention contemplates a conductor substrate 10 comprising a layer of stainless steel or Haynes 25 laminated with one or more layers of copper. In some embodiments, the present invention contemplates a conductor substrate comprising a core layer of stainless steel or Haynes 25 laminated between two layers of copper.

Geometry of Surgical Tips

In one aspect, the present invention provides improved surgical tip geometries that provide improved tissue compression area and hence improved hemostatis. In some aspects, the present invention provides a surgical tip having a planar spatula shape, for example, having a greater cross sectional area than the thickness of the substrate.

It should be appreciated that while the figures show a surgical tip having a simple rounded shape (FIG. 1A), wide rounded shape (FIG. 1B) and pointed shape (FIG. 1C), the conductor tip may have any other geometry suitable for its intended purpose. For instance, the conductor may also be shaped such that it has an oval, triangular, square or rectangular cross-section. Various tip configurations are shown, for example, in FIGS. 1A, 1B and 1C.

The ferromagnetic coating may be between a first section (or proximal portion) and a second section (or distal portion) of the conductor. This may provide the advantage of limiting the active heating to a small area, instead of the entire conductor. A power supply may also connect to the first and second section to include the ferromagnetic coating within a circuit providing power.

In addition, the present invention also contemplates geometries that may be used in a shearing tool, such as scissors, a sealing/cutting clamp, and the like.

Manufacturing Methods

In accordance with the present invention, a flat surgical tip tool heating element of any shape desired can be manufactured by any one of various suitable methods, including chemical etching, stamping, machining, or by electro-deposition from a metal sheet. This provides flexibility to optimize the tool geometry to provide a broader hemostatic surface(s). While beryllium copper (BeCu) is the preferred material, given its ease of plating, electrical and thermal properties, good formability, and low cost, other materials may also be used, including beryllium copper laminates with copper. Tungsten is an alternative material if significantly greater stiffness is required.

Multiple heating elements can be etched from single sheet. They can be arranged to maximize part density. Multiple units can be manufactured from a single sheet of material to improve plating productivity, as shown in FIGS. 2A and 2B. All of these factors reduce cost. Cleaning and plating these heating elements is also much easier with a BeCu substrate. Once plated, the parts may be coated either with TiAlN for the dissection tools or with a non-stick coating like PTFE, for the cutting and sealing heating elements.

Sheet stock for BeCu is readily available in many thicknesses, including a standard 0.5 mm (0.020 in). The desired element shape is created by commercially available processes like photo etching, stamping and EDM. This allows manufacture of heating elements for dissection or vessel sealing of any shape desired. A typical new dissection tip shape, with a hemostatic pad is shown, for example, in FIGS. 1A, 1B and 1C.

BeCu and many other substrate sheet stock materials are ductile. Consequently the tips made from it, are bendable, particularly between the plated area and the end of the tip extension, as shown in FIGS. 3A and 3B.

The thermal expansion coefficient of BeCu is 16.7 $\mu m/m/°C$. Similarly, Niron has a thermal expansion coefficient of 13.3 $\mu m/m/°C$. These values are similar and will result in less stress between the layers when the parts heat up and cool down. This will reduce the risk of the plating material flaking off of the BeCu substrate.

BeCu has an electrical resistivity of 6.8 $\mu\Omega$-cm versus 5.6 for tungsten. This is a slight increase and has an insignificant impact on the joule heating of the non-plated sections compared to tips of similar geometry made of tungsten.

Sheet material of BeCu is easily plated, requiring less cleaning and preparation and plate more reliably than other materials, such as tungsten wire. In addition, etched parts are easily organized into multi element combs which can be plated as a single entity, as shown in FIGS. 2A and 2B. This may improve the consistency of plating depth and reduce the time and labor involved in the plating process.

Etching the parts may also provide a sharper leading edge compared to a round wire, where, for example, the edge is only partially or gradually etched away. This may reduce drag when the tool is pulled through tissue. Additional surface contact area may also play a part.

The cost of etching parts from BeCu is significantly less than the cost of bending tungsten wire and virtually eliminates the potential for the material to break due to bending. This combined with the simplicity of plating, make these heating elements less expensive than plated tungsten wire.

In some embodiments, suitable for sealing and dividing tissue, the shape of a heating element is a broad 1-2 mm wide part with a formed convex surface. This is easily accomplished by etching and then forming the parts.

Stiffness is advantageous when the user wants to use the heating element's structure to pry or blunt dissect tissue. BeCu has a modulus of elasticity of 130 GPa versus 400 GPa for tungsten. As deflection of a beam is inversely proportion to the modulus of elasticity, a piece formed from BeCu would be expected to be 1/3 as stiff as Tungsten at the same dimensions. This can be overcome somewhat by thickening the material, increasing the leg width, shortening the legs, or using carefully designed cross-sectional geometries.

The higher the material's thermal conductivity, the faster it will drain off heat when it is deactivated. In practice moderately good conduction is desirable, as cooling by convection into the air is fairly slow process. The thermal conductivity of BeCu is 120 W/m K which is 31% less than tungsten at 174 W/mK. This difference may slow the conduction of heat out of the heating element assuming the same cross sectional dimensions as a 0.5 mm wire. Since heat flow is proportional to the cross-sectional area and the thermal conductivity, simply increasing the cross-sectional area to compensate for the loss in conductivity would alleviate this concern. Since it is advantageous to go well beyond the cross sectional area of the tungsten wire for structural reasons, thermal conductivity may not be an issue. An alternative substrate material is titanium, which has a lower thermal conductivity at 121 W/mK but has good stiffness. A coating layer of copper, which has a thermal conductivity of 400 W/m K, could be used to improve the thermal bleed off back into the tool's structure.

The higher the heat capacity by volume of the heating element, the more heat needs to be drained from the part. Tungsten has a volumetric heat capacity of $2.5 \times 10^3$ KJ/m$^3$ K. Titanium has a similar volumetric heat capacity of $2.4 \times 10^3$ KJ/m$^3$ K. BeCu has a volumetric heat capacity of $3.47 \times 10^3$ KJ/m$^3$ K. This is 39% greater than tungsten and the part will store more heat energy and cool off slower unless a better conduction path is provided. Combined with the lower thermal conductivity of the material we would need legs with 1.8× the cross sectional area for the BeCu substrate than the 0.5 mm diameter tungsten wire to attain the same thermal drainage rate and cool down time.

Suitable photo chemical etching or photo chemical milling processes are well known in the industry. Such processes are similar to printed circuit board fabrication processes. Examples of suitable process include processes utilized by such companies as Tech-Etch, FotoFab, United Western Enterprises, Kem-Mil-Co, and Elcon Precision.

Generally, such processes include the step of creating a design for the etched part, which is sent to an etching supplier in the form of a 2D line drawing computer file. The file shows the outline of the part, any holes, and bend or score lines, if any. The sheet material to be used is also specified, including thickness, temper or heat treatments, and any special instructions. The company creates a photo stencil or photo tool from the computer file. There are usually two stencils—a front and a back. The metal sheet that will make the finished parts is cleaned and a photoresistive layer is laminated to both front and back surfaces of the metal sheet. This photoresist is sensitive to light. The stencils are placed on the front and back of the metal sheet over the photoresist. A light is shined through the stencils on to the photoresist. The photoresist hardens into an acid resistant film where the light strikes the photoresist. The unexposed photoresist areas are washed away. The metal sheet with the photoresist laminates on both sides is sprayed or immersed in an acid bath that eats away any of the bare metal areas, leaving metal intact where the photoresist was applied. The remaining photoresist is cleaned from the etched sheet. The finished parts are broken out of the surrounding frame, and bent or formed into a final shape if that was specified for the particular part.

The etched parts are cleaned and then plated with a ferromagnetic alloy where heat is to be generated. This plated component is then over coated with a protective layer such as TiAlN, TiN, gold plating, PTFE or other materials, provided by outside processors. The plated product is then assembled into a finished dissection tip or a shear tool.

In some embodiments, the etching process produces a semi-circular cavity on the upper and lower sides of the substrate that connect to form a sharpened edge in the middle, similar to the shape of a curved bracket "}".

There is thus disclosed an improved thermally adjustable surgical tool. It will be appreciated that numerous changes may be made to the present invention without departing from the scope of the claims.

The invention claimed is:

1. An apparatus, comprising:
   a tab having an edge; and
   a plurality of surgical dissection tip substrates, each of the plurality of surgical dissection tip substrates including:
      a tip having a proximal end, a distal end, and opposing first and second planar surfaces having a same width across the proximal end and a same length between the proximal end and the distal end, the length of the first and second planar surfaces being greater than a thickness of the dissection tip substrate;
      two substantially parallel planar extension strips having respective first ends directly connected to the edge of the tab, and respective second ends, opposite to the first ends, connected to the proximal end of the tip, the first ends of the planar extension strips being spaced apart from one another and the second ends of the planar extension strips being spaced apart from one another, wherein the tip and the planar extension strips are on a same plane, and the two planar extension strips have respective lengths between the first ends and the second ends of the planar extension strips that is greater than the length of the first and second planar surfaces of the tip, each of the two planar extension strips being directly connected to both the first and the second planar surfaces of the tip; and
      a ferromagnetic layer coating at least a portion of each of the first and second planar surfaces of the tip.

2. The apparatus of claim 1, wherein the plurality of surgical dissection tip substrates include beryllium copper.

3. The apparatus of claim 2, wherein the beryllium copper comprises greater than 1 percent by weight beryllium.

4. The apparatus of claim 2, wherein the beryllium copper comprises greater than 1.5 percent by weight beryllium.

5. The apparatus of claim 2, wherein the beryllium copper comprises about 2 percent by weight beryllium.

6. The apparatus of claim 1, wherein the surgical dissection tip substrates include beryllium copper laminated to at least one layer of copper.

7. The apparatus of claim 6, wherein the surgical dissection tip substrates include beryllium copper laminated between two layers of copper.

8. The apparatus of claim 1, wherein the ferromagnetic coating comprises a ferromagnetic alloy.

9. The apparatus of claim 1, wherein the ferromagnetic coating comprises a nickel iron alloy.

10. A surgical dissection tip, comprising:
    a beryllium copper substrate having a thickness, the substrate including:
       a beryllium copper planar tip having a proximal end, a distal end, and opposing first and second planar surfaces having a same width across the proximal end and a same length between the proximal end and the distal end, the length of the first and second planar surfaces being greater than the thickness of the substrate, and
       two planar extension strips having distal ends connected to the proximal end of the planar tip, the distal ends of the planar extension strips spaced apart from one another and the proximal ends of the planar extension strips spaced apart from one another, wherein the planar tip and the planar extension strips are on a same plane, and the two planar extension strips have respective lengths between the distal ends and the proximal ends of the planar extension strips that is greater than the length of the first and second planar surfaces of the planar tip, each of the two planar extension strips being directly connected to both the first and the second planar surfaces of the beryllium copper planar tip; and a ferromagnetic layer coating at least a portion of each of the first and second planar surfaces of the beryllium copper planar tip.

11. The surgical dissection tip of claim 10, wherein the two planar extension strips are substantially parallel.

12. The surgical dissection tip of claim 10, wherein the planar extension strips have a width in the plane of the extension strips, wherein the width of each extension strip is greater than the thickness of the substrate.

13. The surgical dissection tip of claim 10, wherein the surgical dissection tip comprises a raised portion in between two recessed portions.

14. A method for manufacturing a surgical dissection tip, comprising:
forming a substrate comprising beryllium copper, wherein the substrate comprises a planar tip having a proximal end, a distal end, and opposing first and second planar surfaces having a same width across the proximal end and a same length between the proximal end and the distal end, the length of the first and second planar surfaces being greater than a thickness of the substrate, and two planar strips having distal ends extending from the proximal end of the tip, the distal ends of the planar strips spaced apart from one another, and the proximal ends of the planar strips spaced apart from one another, the two planar strips having respective lengths between the distal ends and the proximal ends of the planar strips that is greater than the length of the first and second planar surfaces of the tip, each of the two planar strips being directly connected to both the first and the second planar surfaces of the planar tip, wherein the tip and the planar strips are on a same plane; and
coating at least a portion of each of the first and second planar surfaces of the planar tip with a ferromagnetic layer, subsequent to the forming the substrate.

15. The method of claim 14, wherein the two planar strips are substantially parallel.

16. The method of claim 14, wherein the substrate comprising beryllium copper is formed by a process comprising electrodeposition.

17. The method of claim 14, wherein the thickness of the substrate is from about 0.3 mm to about 1.5 mm.

18. A method for manufacturing a surgical dissection tip, comprising:
providing a planar sheet of substrate material, the planar sheet having a thickness;
removing a portion of the sheet of substrate material to form a planar tip having a proximal end, a distal end, and opposing first and second planar surfaces having a same width across the proximal end and a same length between the proximal end and the distal end, the length of the first and second planar surfaces being greater than the thickness of the planar sheet, and two planar strips having distal ends extending from the proximal end of the tip, the distal ends of the planar strips spaced apart from one another, and the proximal ends of the planar strips spaced apart from one another, the two planar strips having respective lengths between the distal ends and the proximal ends of the planar strips that is greater than the length of the first and second planar surfaces of the tip, each of the two planar strips being directly connected to both the first and the second planar surfaces of the planar tip, wherein the tip and the planar strips are on a same plane; and
coating at least a portion of each of the first and second planar surfaces of the planar tip with a ferromagnetic layer, subsequent to the removing the portion of the sheet of substrate material to form the planar tip.

19. The method of claim 18, wherein the planar sheet of substrate material comprises beryllium copper.

20. The method of claim 18, wherein the two planar strips are substantially parallel.

21. The method of claim 18, wherein the portion of the sheet of substrate material is removed by a process comprising etching.

22. The method of claim 18, wherein the portion of the sheet of substrate material is removed by a process comprising cutting.

23. The method of claim 18, wherein the planar tip has a central region and an edge and a thickness of the central region is greater than a thickness at the edge to provide a sharper edge for cutting.

24. The method of claim 18, wherein the thickness of the planar sheet is from about 0.3 mm to about 1.5 mm.

25. The method of claim 18, wherein the planar strips have a width in the plane of the extension strips, wherein the width of each extension strip is greater than the thickness of the planar sheet.

26. The method of claim 18, wherein the planar tip has a width in the plane of the planar sheet of substrate material and a thickness in a plane perpendicular to the plane of the planar tip, wherein the width of the planar tip is greater than the thickness of the planar tip.

* * * * *